United States Patent [19]

Müller et al.

[11] Patent Number: 5,395,370

[45] Date of Patent: Mar. 7, 1995

[54] VERTEBRAL COMPRESSION CLAMP FOR SURGICAL REPAIR TO DAMAGE TO THE SPINE

[75] Inventors: Walter Müller, Voehringen; Georg Piotrowski, Oberndorf, both of Germany

[73] Assignee: Pina Vertriebs AG, Neuhausen, Switzerland

[21] Appl. No.: 962,265

[22] Filed: Oct. 16, 1992

[30] Foreign Application Priority Data

Oct. 18, 1991 [CH] Switzerland ............... 3055/91

[51] Int. Cl.[6] .................................. A61B 17/56
[52] U.S. Cl. ........................ 606/61; 403/44; 294/101
[58] Field of Search .............. 623/17; 606/61; 294/101, 116; 403/44

[56] References Cited

U.S. PATENT DOCUMENTS

| | | | |
|---|---|---|---|
| 2,226,651 | 12/1940 | York | 294/116 |
| 4,289,123 | 9/1981 | Dunn | 606/61 |
| 4,611,582 | 9/1986 | Duff | 606/61 |

FOREIGN PATENT DOCUMENTS

| | | | |
|---|---|---|---|
| 3802833 | 9/1988 | Germany | 606/61 |
| 1074514 | 2/1984 | U.S.S.R. | 606/61 |
| 1517954 | 10/1989 | U.S.S.R. | 606/61 |

Primary Examiner—David H. Willse
Attorney, Agent, or Firm—McGlew and Tuttle

[57] ABSTRACT

A medical technical compression implant (1) for the surgical repair of damage to the spine, especially in the cervical region, includes two clamp jaws (3, 4), which are directed toward each other, are hook-shaped, are connected by a threaded spindle (2), and can be compressed while reducing the distance (B) between them. A wrench profile (9) for attaching a rotating tool in an interlocking manner is arranged at the threaded spindle (2) between two threaded sections (7, 8) with right-hand threads and left-hand threads, respectively. Both the clamp jaws (3, 4) have threaded nuts (5, 6), which are pivotably mounted from bodies, with diametrical threaded bores for screwing on the threaded sections (7, 8). The threaded nuts are mounted in cylindrical transverse bores of the clamp jaws (3, 4). The bore walls (21) are provided with diametrical openings (22, 23) for passing through the threaded sections (7, 8) of the threaded spindle (2). The threaded spindle (2) has, at both ends, an outwardly tapering cone (12, 13) each, which brings about pivoting of the clamp jaw (3, 4) around the axis of the transverse bore in the pulling direction, in cooperation with the inner edge or inner surface of the opening (22) designed as a radial bore.

A manipulating device in the form of a special expanding forceps is provided for implantation.

9 Claims, 3 Drawing Sheets

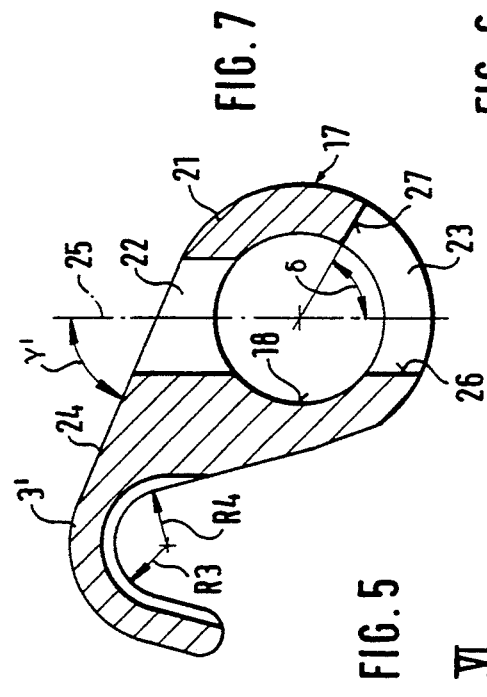
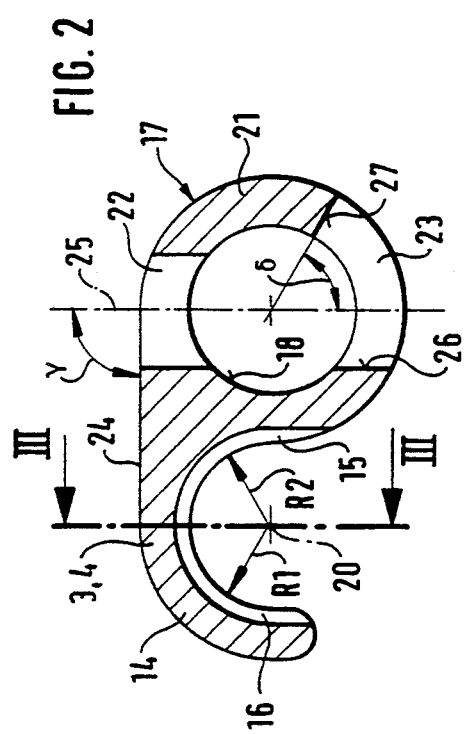
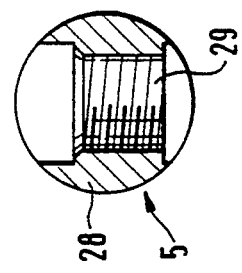
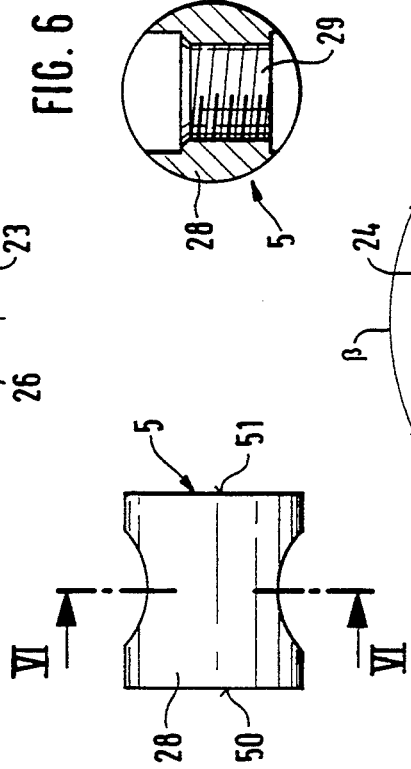
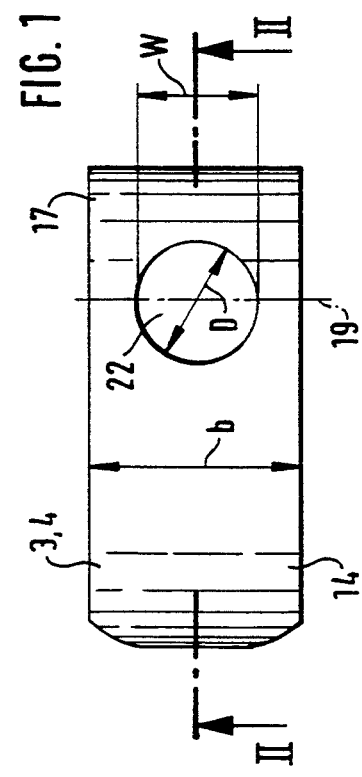
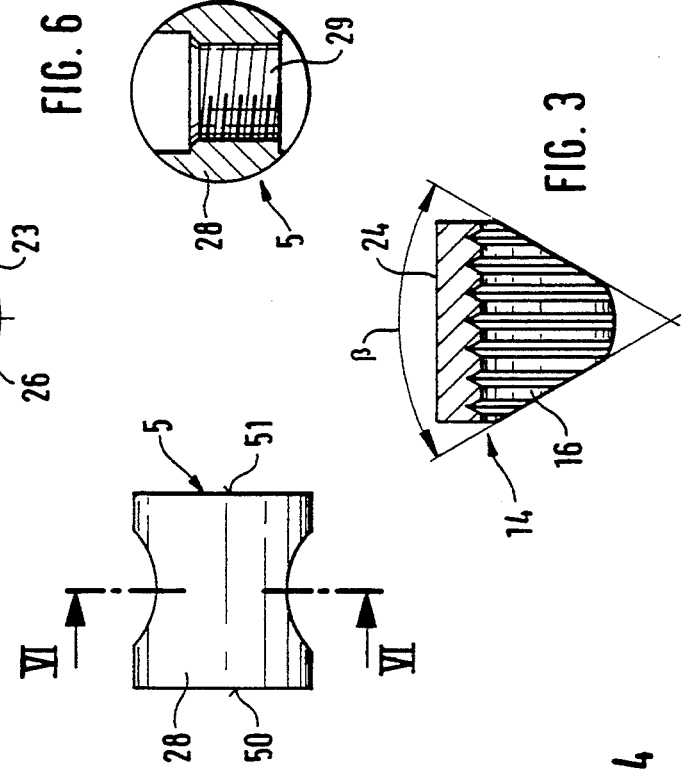
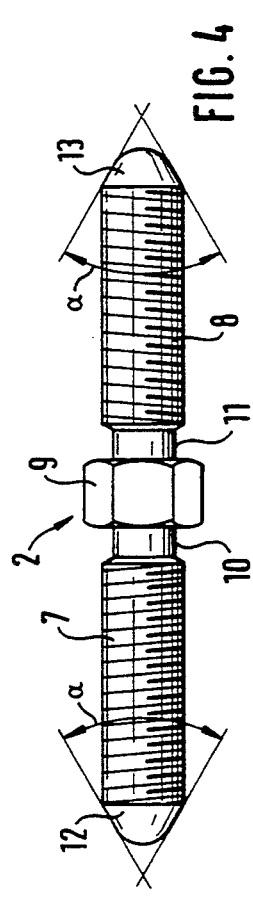

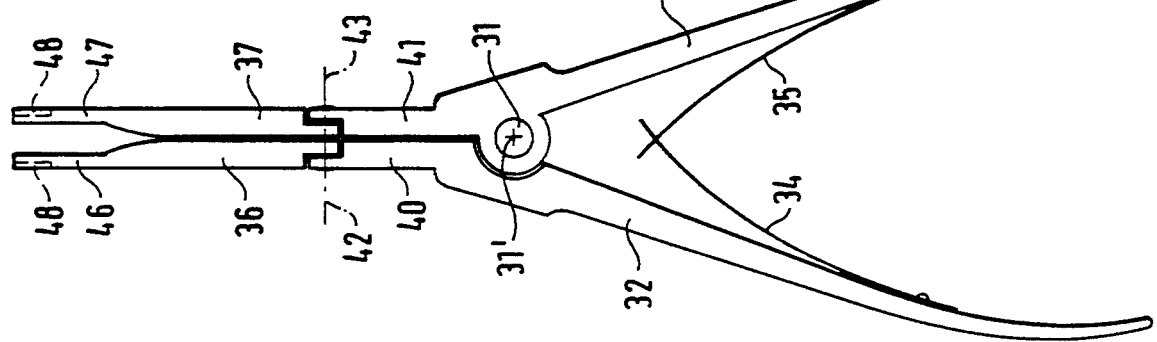

VERTEBRAL COMPRESSION CLAMP FOR SURGICAL REPAIR TO DAMAGE TO THE SPINE

FIELD OF THE INVENTION

The present invention pertains to a medical technical compression implant for the surgical repair of damage to the spinal column, especially in the cervical region, consisting of two clamp jaws, which are bent in the shape of a hook, are directed against each other, are connected by a threaded spindle, and can be contracted by reducing the distance between them, and of a manipulating device for the compression implant.

BACKGROUND OF THE INVENTION

Compression implants of this class are used in surgical medicine, especially in operations for restoring the normal functions of pathologic or injury-related damage to the spinal column.

Curvatures of the spine may be the consequence of, e.g., disturbances of growth, which lead to wedge-shaped changes in the spinal column, or they may be due to tuberculous collapse of individual vertebral bodies. Vitamin D deficiency has also been known to be able to lead to severe rachitic curvatures of the spine, and calcipenia has been known to be able to cause collapse of vertebrae after the menopause. In addition, accident-related vertebral fractures, which must be treated surgically, occur with increasing frequency.

To correct such postural defects or to stabilize these disease-related or traumatic vertebral fractures, individual vertebrae or vertebral prostheses are mutually braced, clamped, or fixed to or with one another in practice. Metal wires have hitherto been used for this purpose in order to stabilize the vertebrae affected or to attach the aforementioned vertebral prostheses to the vertebrae.

Screw clamps, whose jaws can be pushed over two or more vertebrae during the operation and which can be contracted with a conventional set screw, e.g., in the manner of pipe clamps or the like, have been known as well. These jaws have a hook-shaped design. While one jaw is provided with a smooth bore for passing through the screw shaft, the second jaw has a bore provided with internal threads, into which the screw can be screwed in order to move the two jaws toward one another, and the screw head is located on the outside at the edge of the smooth bore.

These prior-art clamps are unsatisfactory for several reasons. First of all, it is impossible for a single surgeon to insert such a clamp. In addition, its manipulation is very complicated and, in particular, it requires a large surgical incision opening to permit insertion of such a clamp, because the screw head, which is arranged at one end of the screw to which the rotating tool, e.g., a 90° offset screw driver, must be attached. In addition, the two jaws, must be held individually during rotation, as long as screwing in of the screw is taking place, in order to prevent them from leaving the position required for their proper function. Due to the relatively long span distance and the simple, self-locking thread, a very great number of rotations of the screw are also necessary in order to bring the two jaws to the intended final distance needed for proper function.

SUMMARY AND OBJECTS OF THE INVENTION

It is a primary object of the present invention to provide an improved compression implant of the type described in the introduction, which can be manipulated with greater ease and greater simplicity, and which, in particular, can be implanted without the assistance of a second surgeon, and which requires only a short surgical incision in the patient despite its large span.

This task is accomplished according to the present invention by the threaded spindle having—between two threaded sections, one with right-hand threads and another with left-hand threads—a wrench profile for the interlocking attachment of a rotating tool, and by both clamp jaws having, as threaded nuts, pivotably mounted cylindrical rotary bodies with diametrical threaded bores for screwing in the threaded sections.

Of particular advantage is the use of a threaded spindle provided with threaded sections cut in opposite directions, with obligatorily self-locking threads, because double the amount of change is achieved by one rotation of the spindle compared with the prior-art clamp. In addition, the pivoting mount of the threaded nuts in the two clamp jaws offers the highly advantageous possibility for the clamp jaws to pivot apart additionally when they are located at the ends of the threaded spindle, in order to obtain a larger opening width or span. Due to the fact that the wrench profile of the threaded spindle is located in the middle between the two threaded sections with opposite thread directions, it is also possible to attach the wrench needed for rotating the threaded spindle, e.g., a hexagon head wrench, in the middle of the thread. As a result, the length of the necessary surgical incision can be kept substantially shorter than in the case of the use of the prior-art clamps. The pivoting apart of the clamp jaws may also be performed after introduction into the surgical opening. Another advantage is the fact that two clamp jaws may have completely identical design; a particularly favorable design of the clamp jaws in terms of the pivotability and mounting of the rotary bodies designed as threaded nuts wherein the threaded nuts are mounted in cylindrical transverse bores of the clamp jaws, the clamp jaws having walls with diametrical openings for passing through the threaded section of the threaded spindle. The opening on the inner side of the clamp jaw has an elongated hole which permits the threaded spindle, which passes therethrough and is screwed into the threaded nut, to pivot by at least 15° around the axis of the transverse bore.

A very substantial additional advantage is achieved by the design of the opening located on the outer side of the clamped jaw as a radial bore, with respect to the axis of the transverse bore, and wherein the threaded spindle has an outwardly tapering cone which allows the pivoting of the clamp jaw around the axis of the transverse bore in cooperation with the inner edge or inner surface opening designed as a radial bore. The additional pivoting movement of the two clamp jaws around the axis of the transverse bores permits not only a shorter threaded spindle to be used, but also a greater pulling movement of the two clamp jaws during the initial phase of the screwing in of the threaded spindle into the two threaded nuts to be achieved. This also leads to substantially greater ease of manipulation and to time savings during insertion.

The clamp jaws are preferably of identical design and have a claw each, provided with an approximately semicylindrical inner surface, with a geometric axis of curvature extending at least approximately in parallel to the axis of the transverse bore. The inner surfaces of the claws have grooves or toothed profiles extending in the circumferential direction. The claws are preferably provided with a trapezoidal cross-sectional profile. The inner surface of the claw is provided with two different radii of curvature and the larger radius of curvature is located on the inner side located adjacent to the transverse bore. A semicircular in section of the opening designed as an elongated hole, the end adjacent to the claw, extends coaxially with the diametrically opposed opening designed as a radial bore. The axis of the opening designed as a radial bore forms a right angle with the rear side of the clamp jaw.

Using the manipulating with end section of grippers of an extending forceps, which grippers have a finger-like design, are provided with slots, which are open at their ends, and—in the area of the slots—with a depression on the outer side of the grippers for holding the clamp jaws in interlocking, non-rotatable manner, the compression implant according to the present invention can be inserted and held securely and in correct position in a highly advantageous and especially correctly functioning manner and secured against rotation during the rotary movements of the threaded spindle, and it is guaranteed that the two opposite clamp jaws cannot be displaced in relation to one another. The design of the manipulating device wherein the grippers with the slots and depressions are hinged to fingers of handles, which fingers are laterally pivotable to a limited extent due to a joint and are connected to one another by a hinge, makes it possible, in particular, to achieve a large range of pivoting of the wrench to be attached to the wrench profile, so that the necessary frequency of transposing the wrench can be greatly reduced.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a top view of a clamp jaw according to the invention;

FIG. 2 is a sectional view taken along line II—II from FIG. 1;

FIG. 3 is a claw profile according to a sectional view taken along line III—III from FIG. 2;

FIG. 4 is a top view of a threaded spindle;

FIG. 5 is a lateral view of a threaded nut according to the invention;

FIG. 6 is a sectional view taken along line VI—VI from FIG. 5;

FIG. 7 is a sectional view of another embodiment of the clamp jaw;

FIG. 11 is a lateral view of an implanting forceps for the compression implant according to FIGS. 8 through 10;

FIG. 12 is a perspective representation of the implanting forceps according to FIG. 11 attached to a compression implant;

FIG. 13 is a perspective representation of the end section of a finger-like gripper of the implanting forceps; and FIG. 14 is a sectional view taken along line XIV–XIV from FIG. 13.

DETAILED DESCRIPTION OF THE PREFERRED EMBODIMENT

Figure 10:
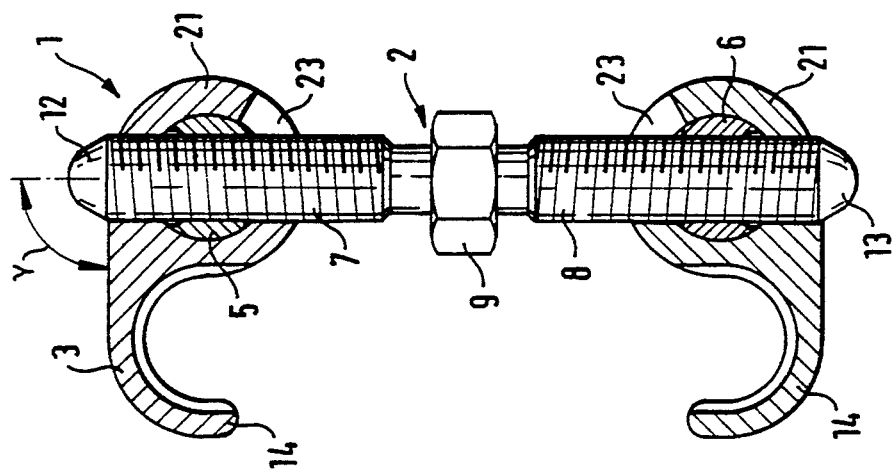
FIG. 10 is a view of the compression implant according to FIGS. 8 and 9, in which the two clamp jaws are in their normal position.
Figure 9:
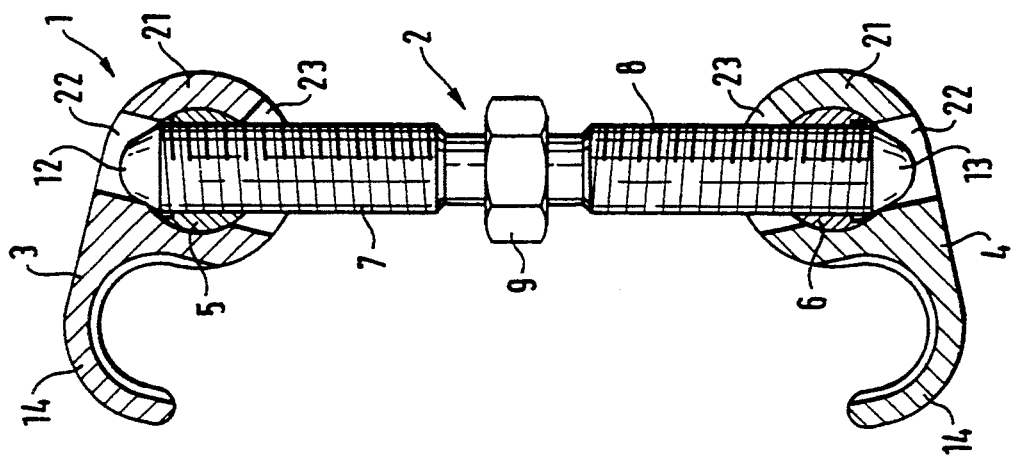
FIG. 9 is a view of the compression implant according to FIG. 8, in which the clamp jaws are located in an only partially pivoted position.
Figure 8:
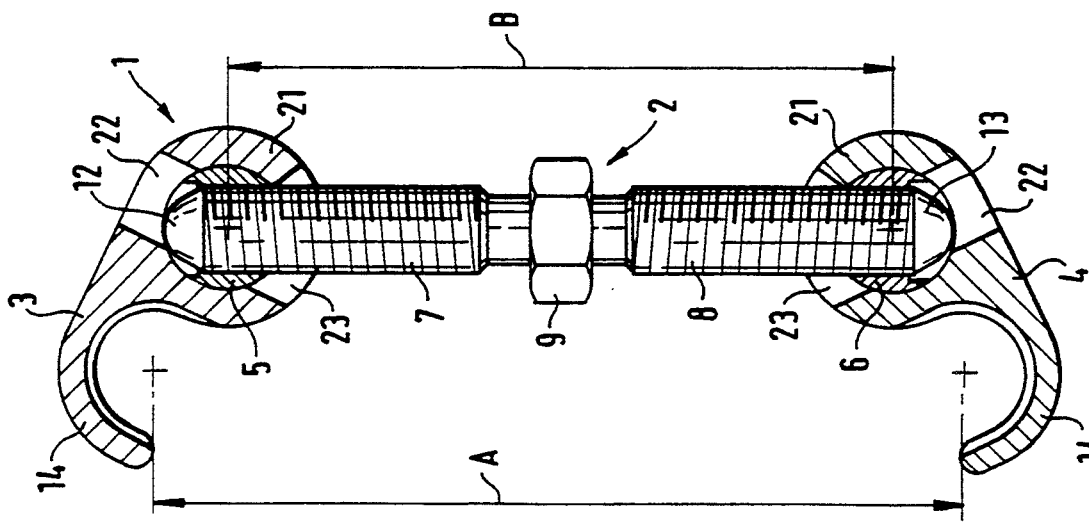
FIG. 8 is a cutaway lateral view of the complete compression implant with the clamp jaws pivoted apart.

The compression implant 1, which is shown in FIGS. 8, 9 and 10, includes of a threaded spindle 2 and two vertebra clamp jaws 3 and 4 of completely identical design, each of which is provided with threaded nuts 5 and 6 mounted pivotably in them.

The threaded spindle 2 shown as a detail in FIG. 4 has a first threaded section 7 with right-hand threads and a second threaded section 8 with left-hand threads. A wrench profile 9, which is separated from the threads of the two threaded sections 7 and 8 by two recesses 10 and 11, is located, in the form of a hexagon, between the two threaded sections 7 and 8. The end-face ends of the threaded sections 7 and 8 are provided with an outwardly tapering, rounded cone 12 and 13 each, which have a cone angle $\alpha$ of about 60°. The two threaded sections 7 and 8 each may be provided with metric threads with a diameter of, e.g., 4 mm.

The two clamp jaws 3 and 4 of identical design are represented as details in FIGS. 1 through 3. Each of them has an approximately semicircular claw 14, whose inner surface 15 is provided with triangular grooves or teeth 16 extending in the circumferential direction, and which has, as a whole, a trapezoidal or wedge-shaped cross-sectional shape with a wedge angle $\beta$ of about 60°. The essentially semicylindrical inner surface 15 of the claw 14 has two different radii of curvature R1, R2, with a common axis of curvature 20, wherein the larger radius of curvature R2 is approximately 6 mm and is located on the inner side adjacent to the transverse bore.

To the claw 14 there is connected around body 17, which is provided with a cylindrical transverse bore 18, whose axis 19 extends in parallel to the axis of curvature 20 of the inner surface 15 of the claw 14. The partially cylindrical wall 21 surrounding the transverse bore 18 is provided with two diametric openings 22 and 23, wherein the upper opening 22 located on the rear side 24 is designed as a radial bore in relation to the bore axis 19, and the lower opening 23 is designed as an elongated hole. The axis 25 of the opening 22, which is designed as a radial bore, which axis intersects the axis 19, is also the axis of curvature for the semicircular end section 26 of the elongated hole 23, while the opposite end section 27, which is likewise semicircular, forms an opening angle 8 of about 60° with the axis 25. With such an opening width, the threaded spindle 2 screwed on can be pivoted by about 30°. The diameter D or the width W of the openings 22 and 23 are each selected to be such that the threaded sections 7 and 8 of the threaded spindle can be passed through freely. In the exemplary embodiment, this width is ca. 4.1 mm.

As is apparent from FIG. 2, the axis 25 of the opening 22 in the clamp jaw 3, 4 shown forms a right angle γ with the flat rear side 24 of the clamp jaw 3, 4. In contrast, FIG. 7 shows another clamp jaw 3', in which the claw 14' has two smaller inner radii R3 and R4, and in which the axis 25 of the opening 22, designed as a radial bore, forms a smaller angle γ' of about 23° with the rear side 24. This the clamp jaw 3' otherwise has the same design as the clamp jaw 3 or 4, so that it can be assembled into a compression implant 1 even with the threaded spindle 2 and the threaded nuts 5 and 6 to be described later, but the span of this compression implant is larger at equal threaded spindle length than in the case of the use of the clamp jaws 3 and 4.

The threaded nuts 5 and 6 are, in principle, of identical design, aside from the direction of their internal threads. As is apparent from FIGS. 5 and 6, they consist of a cylindrical rotary body 28 each with plane-parallel end faces 50, 51, which has, in its axial center, a diametrically extending threaded bore 29, into which either the threaded section 7 with the right-hand threads or the threaded section 8 with left-hand threads of the threaded spindle 2 can be screwed. Consequently, the threaded bore 29 of the threaded nut 5 is provided with right-hand threads, and the threaded nut 6 is provided with left-hand threads. The diameter of the rotary body 28 is adapted to the internal diameter of the transverse bore 18 such that it can easily be introduced into the transverse bore 18 and can be mounted in it rotatably. The length of the rotary body corresponds to the width b of the clamp jaw 3, 4.

In the assembled state, the threaded spindle 2 with its the right-hand threaded section 7, which passes through the lower opening 23 designed as an elongated hole, is screwed into the internal threaded section 28 of the threaded nut 5 to the extent that the rounding of the cone 12 is still located inside the transverse bore 18. In a mirror-inverted manner relative to this, the threaded section 8 with the left-hand thread is screwed analogously into the threaded nut 6 to the same extent, so that the two clamp jaws 3 and 4 can still be pivoted in the outward direction around the axes 19 of their the transverse bores 18 to the extent that the delimiting edges 27 of the end sections of their the openings 23, designed as elongated holes, are in contact with the circumference of the threaded sections 7 and 8, respectively. This position is shown in FIG. 8. It can be recognized that the opening width A of the two gripping clamps 3 and 4 is somewhat larger than the distance B between the axes 19 of the transverse bores 18 in the same position.

In this state, the completely assembled compression implant 1 is placed surgically on the patient's vertebrae which are to be connected to one another, and this expansion of the clamp jaws 3 and 4 can be performed after introduction into the surgical incision. However, it may also be performed prior to introduction, if desired.

During the subsequent rotation of the threaded spindle 2 in the tensioning direction, the expanded position as shown in FIG. 8 will be increasingly reduced, and changed over into the normal position according to FIG. 10, in which the axis of the threaded spindle 2 and the axis 25 of the upper opening 22 extend coaxially with one another, and the threaded spindle 2 also forms a right angle , each with the rear side 24 of the clamp jaw 3 and 4.

This reduction of the expanded position is brought about by the two cones 12 and 13 at the ends of the two threaded sections 7 and 8 penetrating into the openings 32 designed as radial bores and causing, in cooperation with the inner lateral edges or oblique guiding surfaces of the openings 22, the clamp jaws 3 and 4 to pivot in the tensioning direction, so that not only a contraction, i.e., reduction of the distance B between the two clamp jaws 3 and 4, which is brought about by the threads, will take place, but a pivoting movement in the tensioning direction will also be brought about in the area in which the threaded spindle 2 is initially screwed into the two threaded nuts 5 and 6. Consequently, the tensioning effect is substantially stronger in this initial area of tensioning according to FIGS. 8 and 9 than thereafter, when the clamp jaws 3 and 4 assume their angular position shown in FIG. 10 in relation to the axis of the threaded spindle 2.

The implantation of such compression implants 1 can be substantially facilitated with the manipulating device 30 represented in FIGS. 11 through 14, which is in the form of an expanding forceps. It consists of two bent handles 32 and 33, which are hinged to one another by a hinge 31, are pressed against one another by two leaf springs 34 and 35, and are provided with finger-like grippers 36 and 37 each. The grippers 36 and 37 are connected by joints 38 and 39 to fingers 40 and 41 of the handles 32 and 33, respectively, whose respective axes 42 and 43 each extend at right angles to the hinge axis 31'. Due to stop surfaces 44 and 45 on the respective fingers 40 and 41 and on the respective grippers 36 and 37, the grippers 36 and 37 can be pivoted, to a limited extent, in both directions by about 15° each from a central position aligned with the fingers 40 and 41, so that they are able to occupy approximately the position shown in FIG. 12 in one of the end positions.

The end sections 46 and 47 of the grippers 36 and 37 are each designed in a mirror-inverted manner, and each of them is provided with depressions 48, which have the cross-sectional shape of a cylinder section and into which a U-shaped slot 49 each, which is open at the front end, leads. This shaping of the end sections 46 and 47 makes it possible to place these end sections, in the manner shown in FIG. 12, on the clamp jaws 3 and 4, which had already been screwed onto the threaded spindle 2 according to FIG. 8, from the inside, so that the clamp jaws 3 and 4 will be held nonrotatably in an interlocking manner, and will occupy mutually parallel positions.

Using this the manipulating device 30, a surgeon will be able to easily implant the compression implant 1 according to the present invention without the assistance of a second person. Due to the two clamp jaws 3 and 4 being nonrotatably held in the end sections 46 and 47 of the grippers 36 and 37, it is also easy to rotate the threaded spindle 2 in the desired direction by applying a hexagon head wrench on the hexagon 9, so that compression, i.e., bringing together of the two clamp jaws 3 and 4, will be achieved.

It is also conceivable to screw the two clamp jaws 3 and 4 onto the threaded spindle 2 such that their the claws 14 will be directed to the outside, so that expansion rather than compression of vertebrae can be brought about.

While specific embodiments of the invention have been shown and described in detail to illustrate the application of the principles of the invention, it will be understood that the invention may be embodied otherwise without departing from such principles.

What is claimed is:

1. Medical technical compression implant for surgical repair of damage to the spine, comprising:

first and second vertebral clamp jaws, each with a hook-shaped portion sized to be applied over a vertebra and each with a cylindrical transverse bore;

first and second threaded nuts, each of said threaded nuts being pivotably mounted in said cylindrical transverse bore of one of said first and second jaws to each form a cylindrical rotary body, said threaded nuts each having a diametrical threaded bore, extending radially with respect to said cylindrical transverse bore;

a threaded spindle connecting said clamp jaws with hook-shaped portions facing each other, said threaded spindle having a wrench profile for attaching a rotating tool in an interlocking manner between a first threaded section and a second threaded section, said first threaded section having right hand threads and said second threaded section having left hand threads, said clamp jaws having walls surrounding said transverse bores with diametrical openings for passing through said threaded sections of said threaded spindle, said diametrical openings including an inner side opening formed as an elongated hole defining a pivot region for said threaded spindle.

2. Compression implant according to claim 1, wherein: said threaded spindle passes through said elongated hole, and is screwed into said threaded nut, said elongated hole pivot region allowing said thread spindle, screwed into said nut, to pivot by at least 15° around a central axis of said transverse bore.

3. Compression implant according to claim 2, wherein:

said diametrical openings include an outer side opening formed as a radial bore to said central axis of said transverse bore, said threaded spindle having at least one end, an outwardly tapering cone allowing pivoting of said clamp jaw, around said central axis of said transverse bore in a pulling direction, in cooperation with an inner edge of said outer opening formed as a radial bore.

4. Compression implant according to claim 2, wherein:

said two clamp jaws are formed of a substantially identical design with a claw provided with an approximately semicylindrical inner surface with a geometric axis of curvature extending at least approximately in parallel to said axis of said transverse bore.

5. Compression implant according to claim 4, wherein:

inner surfaces of said claws have grooves or tooth profiles extending in a circumferential direction.

6. Compression implant according to claim 4, wherein:

said claw has a trapezoidal cross-sectional profile.

7. Compression implant according to claim 4, wherein:

an inner surface of said claw has two different radii of curvature including a larger radius of curvature located on an inner side adjacent to said transverse bore.

8. Compression implant according to claim 3, wherein:

a semicircular end section of said inner opening, said end section being adjacent to said claw, extends coaxially with said outer opening designed as a radial bore.

9. Compression implant according to claim 2, wherein:

an axis of said inner opening forms a right angle with a rear side surface of said clamp jaw.

* * * * *